United States Patent
Shiah et al.

(10) Patent No.: US 12,414,938 B2
(45) Date of Patent: Sep. 16, 2025

(54) OPHTHALMIC TOPICAL CREAM COMPOSITIONS AND METHODS

(71) Applicant: GLAUKOS CORPORATION, Aliso Viejo, CA (US)

(72) Inventors: James Jane-Guo Shiah, Irvine, CA (US); Xiaojun Michael Liu, Lake Forest, CA (US); Gabriella Szekely, Irvine, CA (US)

(73) Assignee: GLAUKOS CORPORATION, Aliso Viejo, CA (US)

( * ) Notice: Subject to any disclaimer, the term of this patent is extended or adjusted under 35 U.S.C. 154(b) by 0 days.

(21) Appl. No.: 18/304,263

(22) Filed: Apr. 20, 2023

(65) Prior Publication Data

US 2023/0381145 A1    Nov. 30, 2023

Related U.S. Application Data

(60) Provisional application No. 63/363,356, filed on Apr. 21, 2022.

(51) Int. Cl.
| | | |
|---|---|---|
| *A61K 31/4178* | (2006.01) | |
| *A61K 9/00* | (2006.01) | |
| *A61K 9/06* | (2006.01) | |
| *A61K 47/26* | (2006.01) | |
| *A61K 47/32* | (2006.01) | |

(52) U.S. Cl.
CPC ........ *A61K 31/4178* (2013.01); *A61K 9/0014* (2013.01); *A61K 9/06* (2013.01); *A61K 47/26* (2013.01); *A61K 47/32* (2013.01)

(58) Field of Classification Search
CPC ........ A61K 9/0014; A61K 9/06; A61K 47/26; A61K 47/32
See application file for complete search history.

(56) References Cited

U.S. PATENT DOCUMENTS

| | | | |
|---|---|---|---|
| 9,034,830 B2 | 5/2015 | Nanduri et al. | |
| 2012/0195969 A1 | 8/2012 | Riordan et al. | |
| 2016/0136080 A1 | 5/2016 | Sengupta et al. | |
| 2017/0087199 A1 | 3/2017 | Patron et al. | |
| 2017/0266289 A1* | 9/2017 | Lipari | A61Q 19/00 |
| 2018/0318313 A1 | 11/2018 | Sengupta et al. | |
| 2019/0282538 A1* | 9/2019 | Saha | A61K 9/0014 |
| 2020/0188517 A1 | 6/2020 | Shanler et al. | |
| 2022/0071924 A1 | 3/2022 | Arkin et al. | |

FOREIGN PATENT DOCUMENTS

| | | | | |
|---|---|---|---|---|
| CN | 113164452 A | * | 7/2021 | .......... A61K 31/138 |
| JP | 2019524892 A | | 9/2019 | |
| WO | WO-2020141482 A1 | * | 7/2020 | .......... A61K 31/351 |
| WO | 2020/183322 A1 | | 9/2020 | |
| WO | 2024/026365 A1 | | 2/2024 | |

OTHER PUBLICATIONS

SDS Data sheet: Carbopol 980 NF Polymer, Rivion Date Aug. 25, 2018 (Year: 2018).*
SDS Data sheet: SEPINEO P600, Rivision Date Oct. 1, 2021 (Year: 2021).*
Hasanzadeh, Bashir, "Testing and modeling of the thixotropic behavior of cementitious materials." Electronic Theses and Dissertations. Paper 2868. (Year: 2017).*
Al-Kinani, Ali A., et al. "Ophthalmic gels: Past, present and future." Advanced drug delivery reviews 126 (2018): 113-126. (Year: 2018).*
International Search Report and Written Opinion mailed Jul. 27, 2023 for International Application Serial No. PCT/US2023/065956 filed on Apr. 19, 2023.
International Search Report and Written Opinion mailed Nov. 16, 2023 for International Application Serial No. PCT/US2023/071050 filed on Jul. 26, 2023.

\* cited by examiner

*Primary Examiner* — James H Alstrum-Acevedo
*Assistant Examiner* — Justin Christopher Sanchez
(74) *Attorney, Agent, or Firm* — K&L Gates LLP (57) ABSTRACT

An ophthalmic therapeutic treatment composition includes a topical cream containing a crosslinked acrylic acid polymer, an acrylamide/sodium acryloyldimethyl taurate copolymer, and an effective amount of an active pharmaceutical ingredient (API) dispersed in the topical cream. The ophthalmic therapeutic treatment composition and API are formulated for topical application and treatment of various disorders such as dry eye, presbyopia, intraocular pressure and blepharitis.

19 Claims, 5 Drawing Sheets

OPHTHALMIC TOPICAL CREAM COMPOSITIONS AND METHODS

INCORPORATION BY REFERENCE TO ANY PRIORITY APPLICATIONS

This application claims priority to U.S. Provisional Patent Application No. 63/363,356, entitled "OPHTHALMIC TOPICAL CREAM COMPOSITIONS AND METHODS," filed on Apr. 21, 2022, which is hereby incorporated by reference in its entirety and for all purposes.

BACKGROUND

Field

This disclosure relates to ophthalmic therapeutic treatment compositions, processes, and methods of using them to treat disorders and diseases of the eye, particularly by administration to an outer surface of an eyelid of the patient's eye.

Description

Eye drops are the typical way of administrating ophthalmic medications to patients. For example, U.S. Pat. No. 10,610,518 discloses pilocarpine formulations and methods of administering them as eye drops. This route is simple and non-invasive but achieves only limited control over patient's compliance, dose regimen, and duration. Eye drops may lead to undesirable efficacy and clinical results if subjects use them incorrectly. See Souto, E. B., et al., "Advanced Formulation Approaches for Ocular Drug Delivery: State-Of-The-Art and Recent Patents", Pharmaceutics. 2019, 11, 460:1-29. Other ophthalmic formulations have been developed that are said to be suitable for administration by topical application to an outer surface of an eyelid of a subject. See U.S. Pat. No. 9,034,830. However, there remains a need for improved ophthalmic therapeutic treatment compositions and methods.

SUMMARY

Various embodiments provide ophthalmic therapeutic treatment compositions. In an embodiment, an ophthalmic therapeutic treatment composition comprises a topical cream comprising about 0% to about 8% (w/w) of a crosslinked acrylic acid polymer and about 0% to about 8% (w/w) of an acrylamide/sodium acryloyldimethyl taurate copolymer; and an effective amount of an active pharmaceutical ingredient (API) dispersed in the topical cream.

In some embodiments, the ophthalmic therapeutic treatment composition comprises about 0.001% to about 10% (w/w) of the API. In some embodiments, the ophthalmic therapeutic treatment composition comprises about 2% to about 8% (w/w) of the API. In some embodiments, the topical cream comprises about 2% to about 4% (w/w) of the crosslinked acrylic acid polymer. In some embodiments, the topical cream comprises about 2% to about 4% (w/w) of the acrylamide/sodium acryloyldimethyl taurate copolymer.

In some embodiments, the acrylamide/sodium acryloyldimethyl taurate copolymer is dispersed in isohexadecane with polysorbate 80, polysorbate 20, polysorbate 40, or polysorbate 60. In some embodiments, the API comprises pilocarpine. In some embodiments, the ophthalmic therapeutic treatment composition comprises an amount of the API that is effective to alleviate the symptoms of dry eye and/or treat presbyopia. In some embodiments, the API comprises travoprost. In some embodiments, the ophthalmic therapeutic treatment composition comprises an amount of the API that is safe and effective to treat intraocular pressure (IOP). In some embodiments, the API comprises atropine, physostigmine and/or donepezil. In some embodiments, the ophthalmic therapeutic treatment composition comprises an amount of the API that is safe and effective to treat myopia and blepharitis.

In some embodiments, the ophthalmic therapeutic treatment composition has a pH that is in a range of about 3.0 to about 7.8. In some embodiments, the pH of the ophthalmic therapeutic treatment composition is in a range of about 3.5 to about 5.5. In some embodiments, the ophthalmic therapeutic treatment composition has a viscosity in a range of about 4,000 cPs to about 400,000 cPs. In some embodiments, the viscosity of the ophthalmic therapeutic treatment composition is in a range of about 5,000 cPs to about 300,000 cPs. In some embodiments, the ophthalmic therapeutic treatment composition has a viscosity in a range of about 7,500 cPs to about 250,000 cPs.

In some embodiments, the ophthalmic therapeutic treatment composition is thixotropic. In some embodiments, ophthalmic therapeutic treatment composition has less than about 5% (w/w) of degradation of the API when measured after storage at 40° C. for 60 days after preparation of the ophthalmic therapeutic treatment composition. In some embodiments, the ophthalmic therapeutic treatment composition has less than about 10% (w/w) of degradation of the API when measured after storage at 40° C. for 24 months after preparation of the ophthalmic therapeutic treatment composition.

In some embodiments, the ophthalmic therapeutic treatment composition is formulated for application to an outer surface of an eyelid to deliver the API into an eye. In some embodiments, there is less residual of the ophthalmic therapeutic treatment composition after the application of the ophthalmic therapeutic treatment composition to the outer surface of the eyelid compared to application of an otherwise identical composition comprising a hydroxypropyl cellulose (HPC) in place of the acrylamide/sodium acryloyldimethyl taurate copolymer.

In addition, various embodiments provide a method for administering an ophthalmic medicine to a patient's eye. In an embodiment, the method comprises applying an ophthalmic therapeutic treatment composition to an outer surface of an eyelid of the patient's eye, wherein the ophthalmic therapeutic treatment composition comprises a topical cream comprising about 0.5% to about 8% (w/w) of a crosslinked acrylic acid polymer and about 0.25% to about 8% (w/w) an acrylamide/sodium acryloyldimethyl taurate copolymer; and an effective amount of an active pharmaceutical ingredient (API) dispersed in the topical cream.

In some embodiments, the effective amount of the API is about 0.004% to about 10% (w/w). In some embodiments, the API comprises pilocarpine, travoprost, atropine, donepezil or physostigmine. In some embodiments, the method comprises applying the ophthalmic therapeutic treatment composition to the outer surface of the eyelid of the patient's eye at least once per day.

In some embodiments, the method comprises applying the ophthalmic therapeutic treatment composition to the outer surface of the eyelid of the patient's eye up to four times per day. In some embodiments, applying the ophthalmic therapeutic treatment composition to the outer surface of the eyelid of the patient's eye comprises applying with an applicator. In some embodiments, the method further comprises squeezing the ophthalmic therapeutic treatment composition from a container onto the applicator before applying the ophthalmic therapeutic treatment composition to the outer surface of the eyelid of the patient's eye.

DETAILED DESCRIPTION

Ophthalmic therapeutic treatment compositions have now been developed that contain a topical cream that includes about 0.0% to about 8% (w/w) of a crosslinked acrylic acid polymer and about 0.0% to about 8% (w/w) of an acrylamide/sodium acryloyldimethyl taurate copolymer, along with an effective amount of an active pharmaceutical ingredient (API) dispersed in the topical cream. In various embodiments, this polymer combination imparts surprisingly high levels of desirable features to the ophthalmic therapeutic treatment compositions, such as low residuals after application, emoliency, texture and/or storage stability.

Ophthalmic Therapeutic Treatment Compositions

Various embodiments provide an ophthalmic therapeutic treatment composition, comprising:
- a topical cream comprising about 0.0% to about 8% (w/w), such as about 0.05% to about 8% (w/w), of a crosslinked acrylic acid polymer and about 0.0% to about 8% (w/w), such as 0.025% to about 8% (w/w), of an acrylamide/sodium acryloyldimethyl taurate copolymer; and
- an effective amount of an active pharmaceutical ingredient (API) dispersed in the topical cream.

Various suitable crosslinked acrylic acid polymers are commercially available and/or may be readily synthesized by those skilled in the art. In some embodiments, the acrylic acid polymer is a homopolymer of acrylic acid. In other embodiments the acrylic acid polymer is a copolymer primarily comprised of acrylic acid units, along small amounts (typically <10%) of other units formed by copolymerization of acrylic acid with compatible comonomers, such as $C_{10}$-$C_{30}$ alkyl acrylate and/or methacrylic acid. Crosslinking of the acrylic acid polymer may be carried out in various ways, such as by copolymerization with a crosslinking agent such as allyl sucrose or allyl pentaerythritol. In various embodiments, the crosslinked acrylic acid polymer has a molecular weight and degree of crosslinking that results in a solution viscosity (as measured at 0.5 wt % and pH 7.5) that is in a range from about 4,000 cPs to about 80,000 cPs, such as about 40,000 cPs to about 60,000 cPs. Suitable acrylic acid polymers from commercial sources include those available from Lubrizol Corporation under the tradename CARBOPOL®. In a non-limiting example, the crosslinked acrylic acid polymer is Carbomer Homopolymer Type C 980.

The amount of crosslinked acrylic acid polymer in the topical cream is typically in a range of about 0.0% to about 8% (w/w), such as about 0.05% to about 8% (w/w), such as about 0.5% to about 8% (w/w), about 2% to about 6% (w/w), about 2% to about 4% (w/w), or about 3% to about 5% (w/w). The amount of crosslinked acrylic acid polymer may be adjusted based on the viscosity. For example, a suitable amount may be in a range of about 3% to about 5% (w/w) for a crosslinked acrylic acid polymer having a viscosity in a range of about 40,000 cPs to about 60,000 cPs. Those skilled in the art will appreciate the relationship between viscosity and concentration, such that a higher viscosity crosslinked acrylic acid polymer may be used in smaller amounts, whereas larger amounts of a lower viscosity polymer may be suitable in some embodiments.

Various acrylamide/sodium acryloyldimethyl taurate copolymers are commercially available and/or may be readily synthesized by those skilled in the art. In some embodiments, the acrylamide/sodium acryloyldimethyl taurate copolymer is a copolymer of acrylamide and sodium acryloyldimethyl taurate. In other embodiments, the acrylamide/sodium acryloyldimethyl taurate copolymer may contain small amounts (typically <10%) of other units formed by copolymerization of acrylamide and sodium acryloyldimethyl taurate with compatible comonomers, such as methacrylamide and/or sodium methacryloyldimethyl taurate.

The amount of acrylamide/sodium acryloyldimethyl taurate copolymer in the topical cream is typically in a range of about 0.0% to about 8% (w/w), such as 0.025% to about 8% (w/w), such as 0.25% to about 8% (w/w), about 2% to about 6% (w/w), about 2% to about 4% (w/w), or about 3% to about 5% (w/w). The amount of acrylamide/sodium acryloyldimethyl taurate copolymer may be adjusted based on the viscosity in a similar manner to that discussed above for crosslinked acrylic acid polymer.

Likewise, the types, amounts and the viscosities of the polymer ingredients (e.g., the crosslinked acrylic acid polymer and the acrylamide/sodium acryloyldimethyl taurate copolymer) may be adjusted or selected to impart a desirable rheological property (e.g., viscosity and/or thixotropy) to the ophthalmic therapeutic treatment composition. In an embodiment, the ophthalmic therapeutic treatment composition has a viscosity in a range of about 4,000 cPs to about 400,000 cPs, such as about 5,000 cPs to about 300,000 cPs or about 7,500 cPs to about 250,000 cPs.

In an embodiment, the ophthalmic therapeutic treatment composition is formulated for application to an outer surface of an eyelid to deliver the API into an eye. The ophthalmic therapeutic treatment composition can be formulated to be surprisingly thixotropic. Such a high degree of thixotropy is desirable from a patient compliance perspective because the lower viscosity during flow facilitates squeezing the ophthalmic therapeutic treatment composition from a container onto an applicator before applying the ophthalmic therapeutic treatment composition to the outer surface of the eyelid of the patient's eye. After such application, the higher viscosity developed by the ophthalmic therapeutic treatment composition after application on the eyelid allows it to remain in place, thereby providing the subject with additional time prior to being rubbed into the eye.

Acrylamide/sodium acryloyldimethyl taurate copolymers are typically provided by commercial sources in the form of an emulsion gel. See, e.g., G. Bonacucina, et al., "Characterization and Stability of Emulsion Gels Based on Acrylamide/Sodium Acryloyldimethyl Taurate Copolymer" AAPS PharmSciTech. 2009 June; 10 (2): 368-375. In a non-limiting example, the acrylamide/sodium acryloyldimethyl taurate copolymer is SEPINEO® P 600, available commercially in the form of a concentrated dispersion in isohexadecane with polysorbate 80 from Seppic, an Air Liquide Healthcare subsidiary company.

In various embodiments, the crosslinked acrylic acid polymer and the acrylamide/sodium acryloyldimethyl taurate copolymer are combined to form a topical cream. In addition to common ingredients such as water, the topical cream may include minor amounts of other ingredients useful for manufacturing and/or formulation. Non-limiting examples include oils such as mineral oil and polyoxyl castor oil, glycols such a propylene glycol and polyethylene glycol, alcohols such as sorbitol and cetyl alcohol, parabens such as methyl paraben and propyl paraben, stabilizers such as disodium edetate, salts such as magnesium chloride, pH adjusting agents such as citric acid and sodium hydroxide, etc. Suitable amounts of such minor formulation ingredients are illustrated by the non-limiting examples in Table 1.

TABLE 1

| Ingredient | Amount (% w/w) |
|---|---|
| Pilocarpine hydrochloride | 1-10 |
| Polyoxyl 35 castor oil (Kolliphor ELP) | 2-8 |
| Propylene glycol | 1-6 |
| Cetyl alcohol | 0-3 |
| Polysorbate 80 | 1-5 |
| Mineral oil | 5-20 |
| Sorbitol | 2-10 |
| Polyethylene glycol 8000 | 0-5 |
| Methyl paraben | 0.03-0.45 |
| Propyl paraben | 0-0.1 |
| Caffeine | 0-0.5 |
| Magnesium chloride | 0-0.1 |
| Carbomer Homopolymer Type C 980 | 0-8 |
| Disodium edetate | 0-0.3 |
| Purified water | Balance |
| Sepineo ® P600 | 0-8 |
| Sodium hydroxide (pH adjuster) | q.s. |

Figure 1:
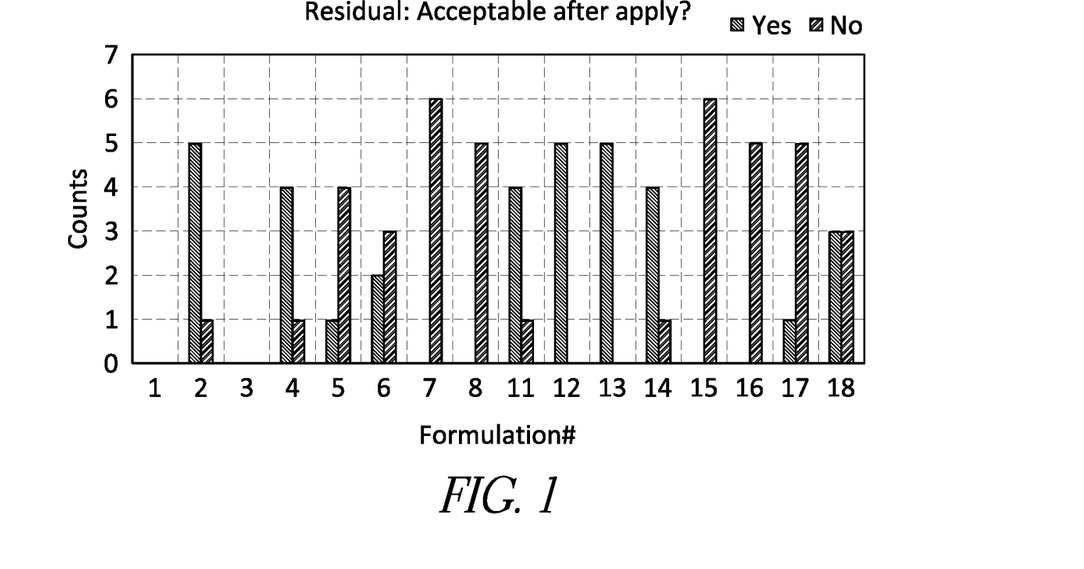
FIG. 1 is a bar graph summarizing survey results from a residuals evaluation of various ophthalmic therapeutic treatment compositions that do not contain acrylamide/sodium acryloyldimethyl taurate copolymer or SEPINEO® P 600 following topical application.

Surprisingly, in some embodiments the combination of crosslinked acrylic acid polymer and acrylamide/sodium acryloyldimethyl taurate copolymer provides unexpectedly high levels of one or more desirable properties that enhance patient acceptance and thus promote patient compliance. For example, FIG. 1 illustrates a bar graph summarizing survey results from a residuals evaluation of various ophthalmic therapeutic treatment compositions following topical application. Table 2 summarizes the primary ingredients and pH of the formulations.

TABLE 2

| No. | Carbomer (wt. %) | HPC (wt. %) | Pilocarpine (wt. %) | PH |
|---|---|---|---|---|
| 1 | 4 | 0 | 4 | 3.5 |
| 2 | 4 | 0 | 4 | 5 |
| 3 | 4 | 0 | 8 | 3.5 |
| 4 | 4 | 0 | 8 | 5 |
| 5 | 4 | 2 | 4 | 3.5 |
| 6 | 4 | 2 | 4 | 5 |
| 7 | 4 | 2 | 8 | 3.5 |
| 8 | 4 | 2 | 8 | 5 |
| 11 | 2 | 0 | 4 | 3.5 |
| 12 | 2 | 0 | 4 | 5 |
| 13 | 2 | 0 | 8 | 3.5 |
| 14 | 2 | 0 | 8 | 5 |
| 15 | 2 | 2 | 4 | 3.5 |
| 16 | 2 | 2 | 4 | 5 |
| 17 | 2 | 2 | 8 | 3.5 |
| 18 | 2 | 2 | 8 | 5 |

Figure 2:
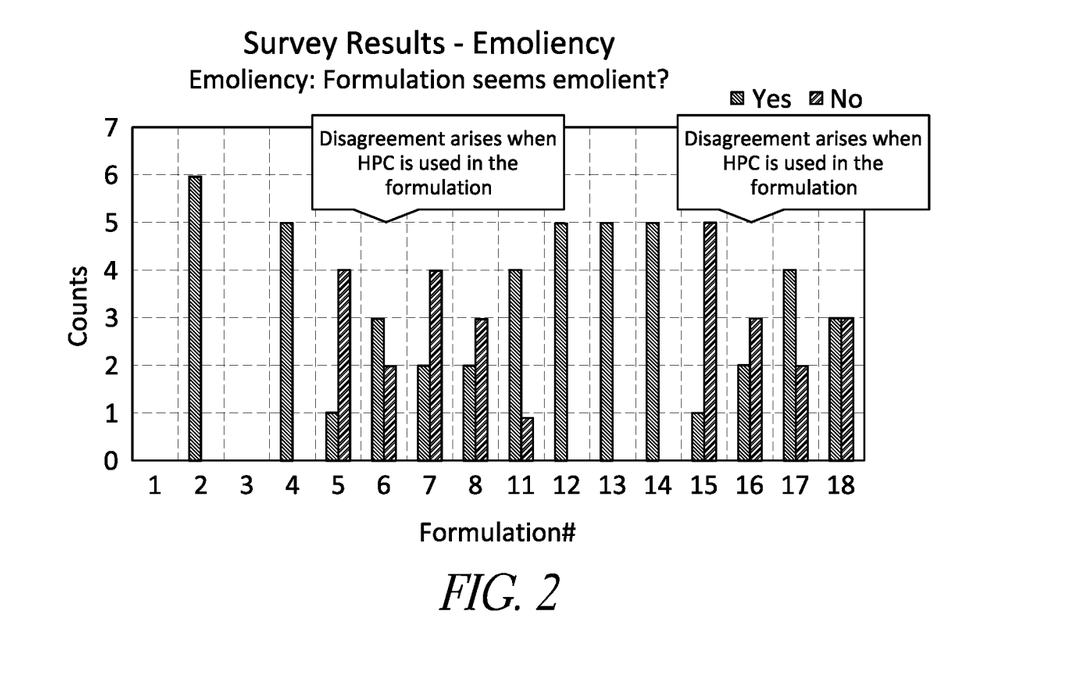
FIG. 2 is a bar graph summarizing survey results from an emoliency evaluation of various ophthalmic therapeutic treatment compositions.
Figure 3:
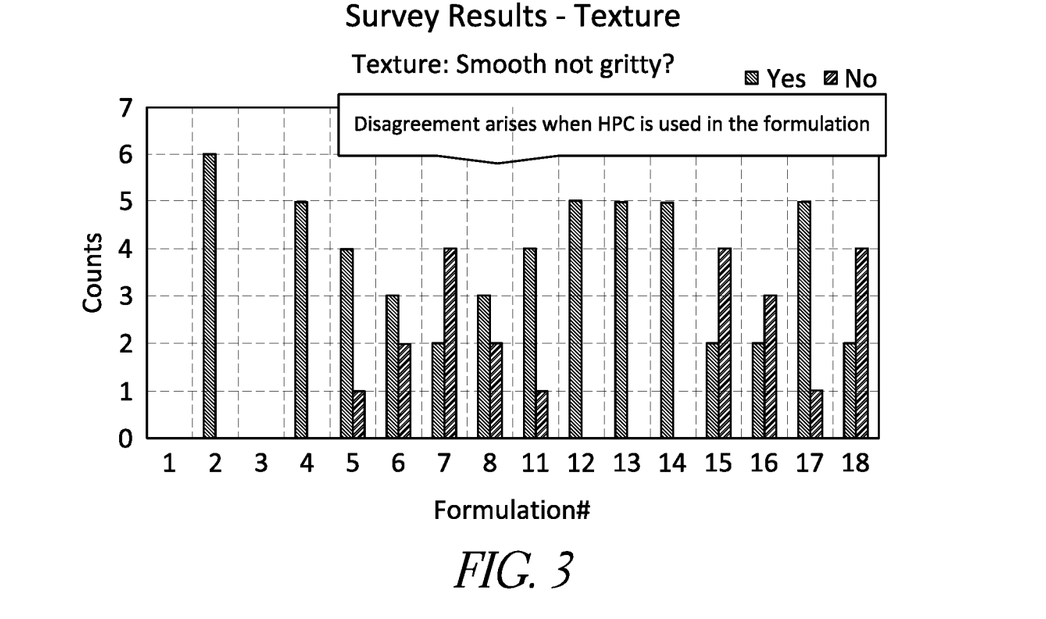
FIG. 3 is a bar graph summarizing survey results from a texture evaluation of various ophthalmic therapeutic treatment compositions.

As shown in Table 2, there is no acrylamide/sodium acryloyldimethyl taurate copolymer or SEPINEO® P 600 present in formulations 1-18. Moreover, there is hydroxypropyl cellulose (HPC) present in formulations 5-11 and 15-18. The data summarized in FIG. 1 shows that topical application of formulations containing a combination of a crosslinked acrylic acid polymer (Carbomer) and hydroxypropyl cellulose (HPC) to the skin of test subjects resulted in the perception of undesirable levels of residuals on skin. Similar trends were observed in evaluations of emollience (FIG. 2) and texture (FIG. 3).

Figure 4:
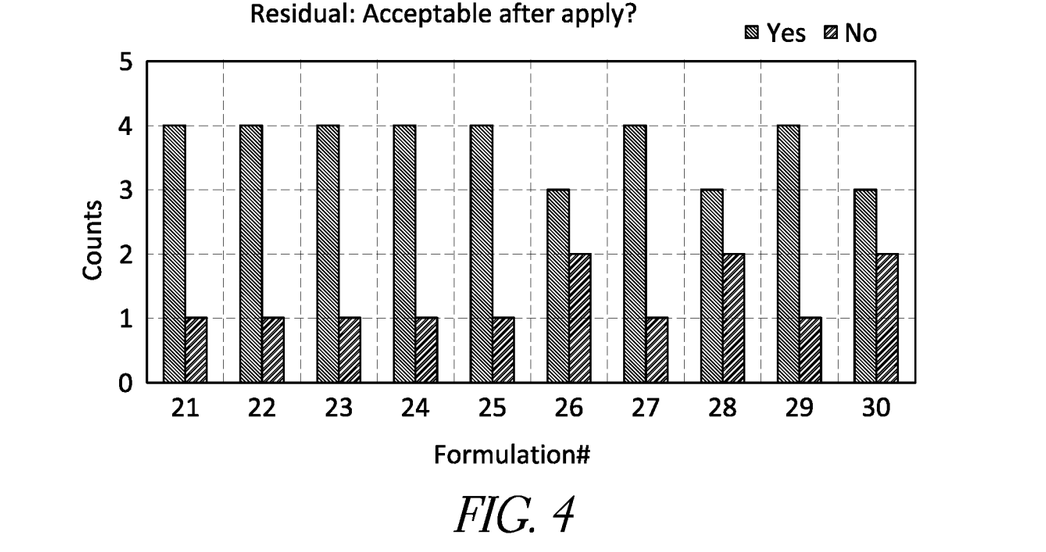
FIG. 4 is a bar graph summarizing survey results from evaluation of the acceptance of residues after application of formulations containing acrylamide/sodium acryloyldimethyl taurate copolymer or SEPINEO® P 600.

In contrast, when the combination with crosslinked acrylic acid polymer includes acrylamide/sodium acryloyldimethyl taurate copolymer in place of HPC, the test subjects report surprisingly higher levels of satisfaction with regard to levels of residuals on skin, emollience and/or texture. The data summarized in FIG. 4 shows that topical application of different formulations containing a combination of crosslinked acrylic acid polymer and acrylamide/sodium acryloyldimethyl taurate copolymer to the skin of test subjects resulted in the perception of much more desirable levels of residuals on skin as compared to HPC (see FIG. 1). Similarly, better evaluations of emollience and texture are observed for formulations containing a combination of crosslinked acrylic acid polymer and acrylamide/sodium acryloyldimethyl taurate copolymer. Table 3 summarizes the primary ingredients and pH of the formulations shown in FIG. 4.

In various embodiments the ophthalmic therapeutic treatment composition has a pH that is in a range of about 3.0 to about 7.8, such as in a range of about 3 to about 5.5, about 3 to about 5, about 3.5 to about 5.5 or about 3.5 to about 5. In an embodiment, the pH is less than 5, e.g., in a range of about 3.0 to less than 5 or about 3.5 to less than 5. For example, in an embodiment, the pH is in a range of about 3.5 to about 4.5. In another embodiment, the pH is in a range of about 3.5 to about 4.

Figure 5:
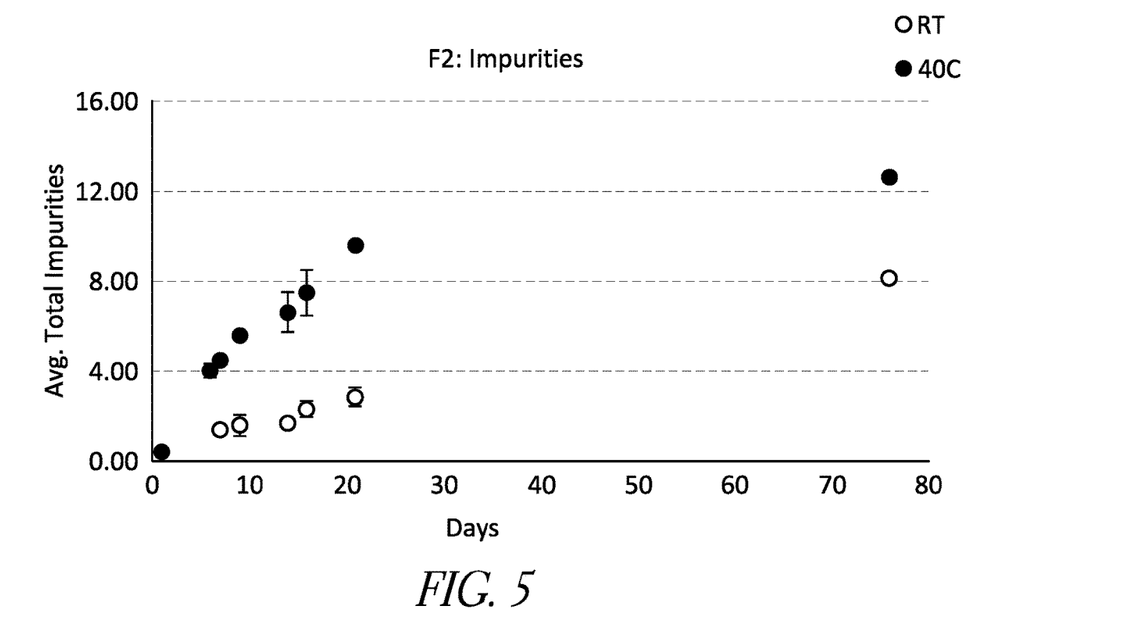
FIG. 5 illustrates stability of an ophthalmic therapeutic treatment composition (F2) having a pH of about 5 as a function of storage time at room temperature and 40° C.
Figure 6:
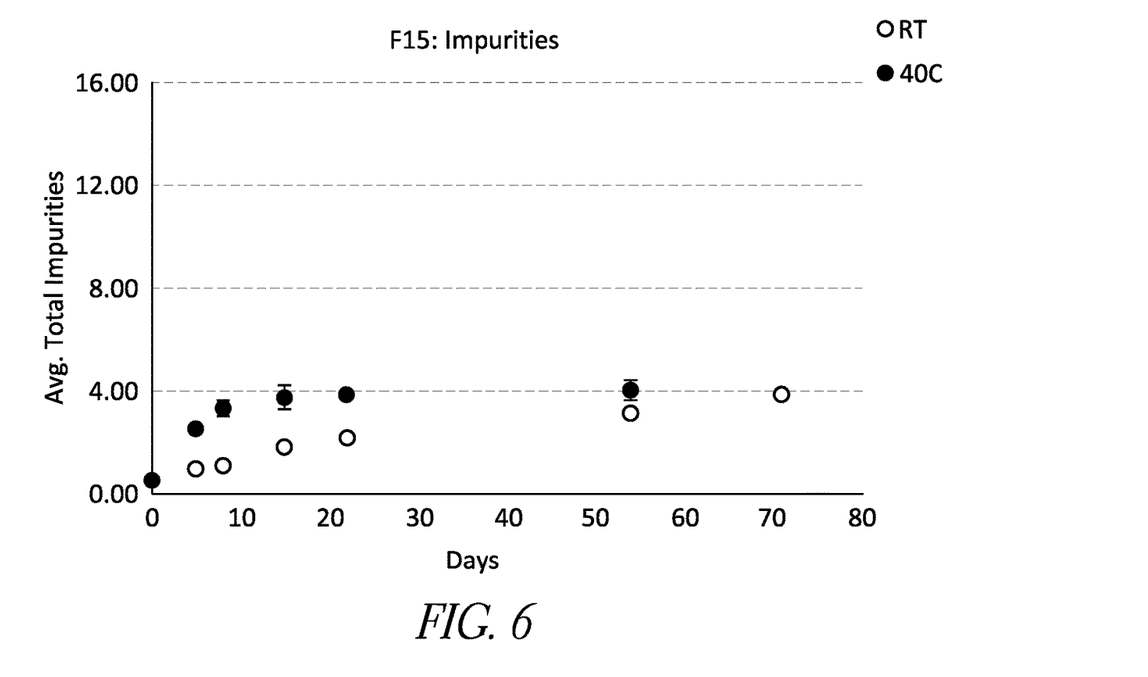
FIG. 6 illustrates stability of an ophthalmic therapeutic treatment composition (F15) having a pH of about 3.5 as a function of storage time at room temperature and 40° C.
Figure 7:
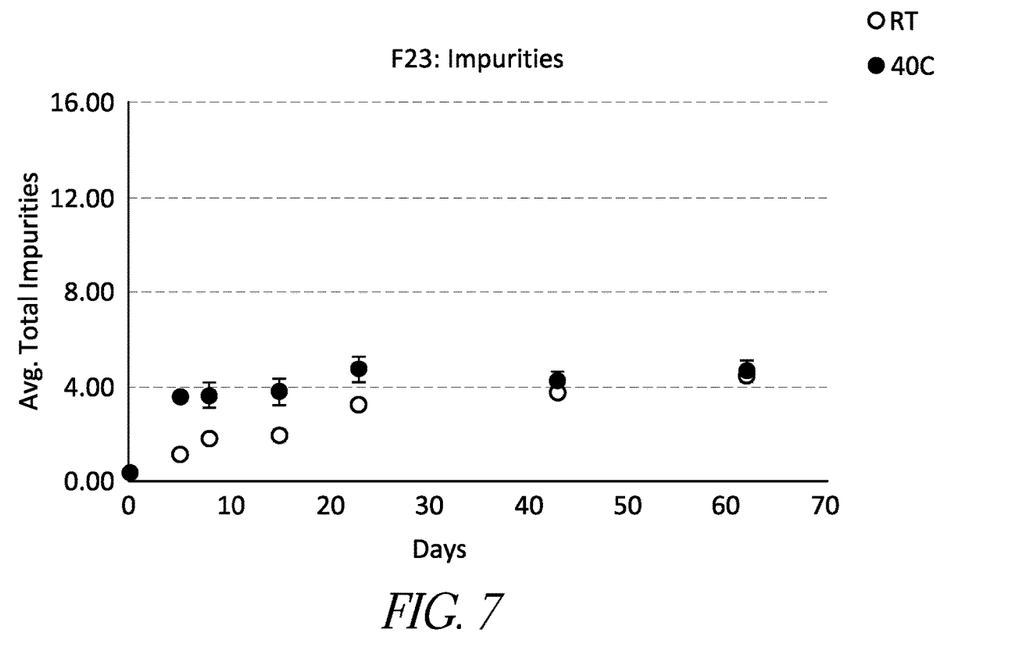
FIG. 7 illustrates stability of an ophthalmic therapeutic treatment composition (F23) having a pH of about 3.5 as a function of storage time at room temperature and 40° C.
Figure 8:
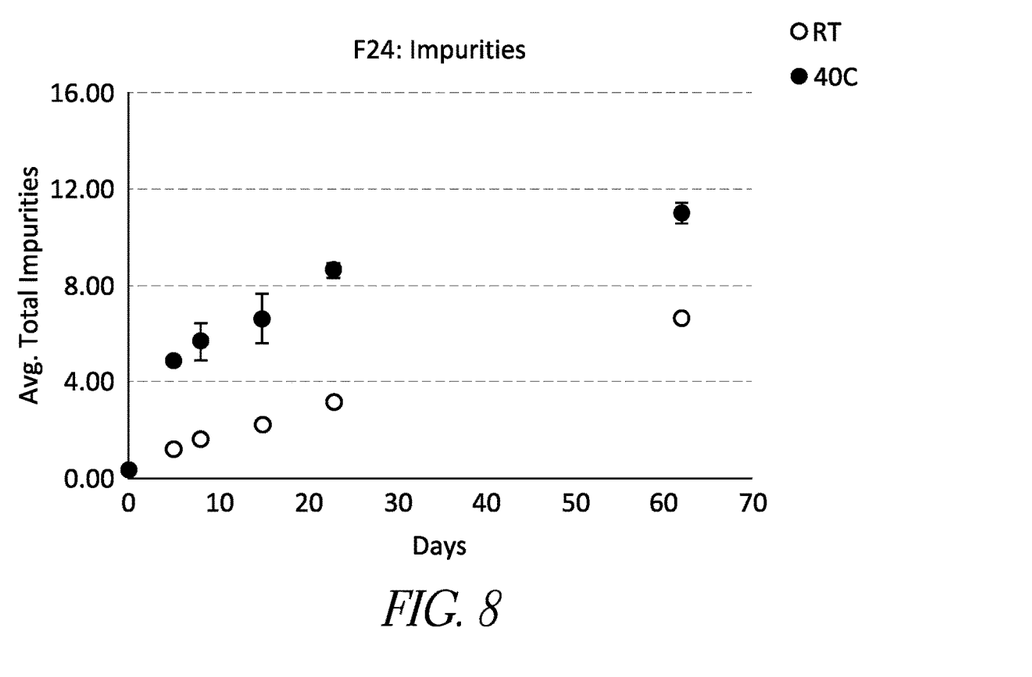
FIG. 8 illustrates stability of an ophthalmic therapeutic treatment composition (F24) having a pH of about 5 as a function of storage time at room temperature and 40° C.
Figure 9:
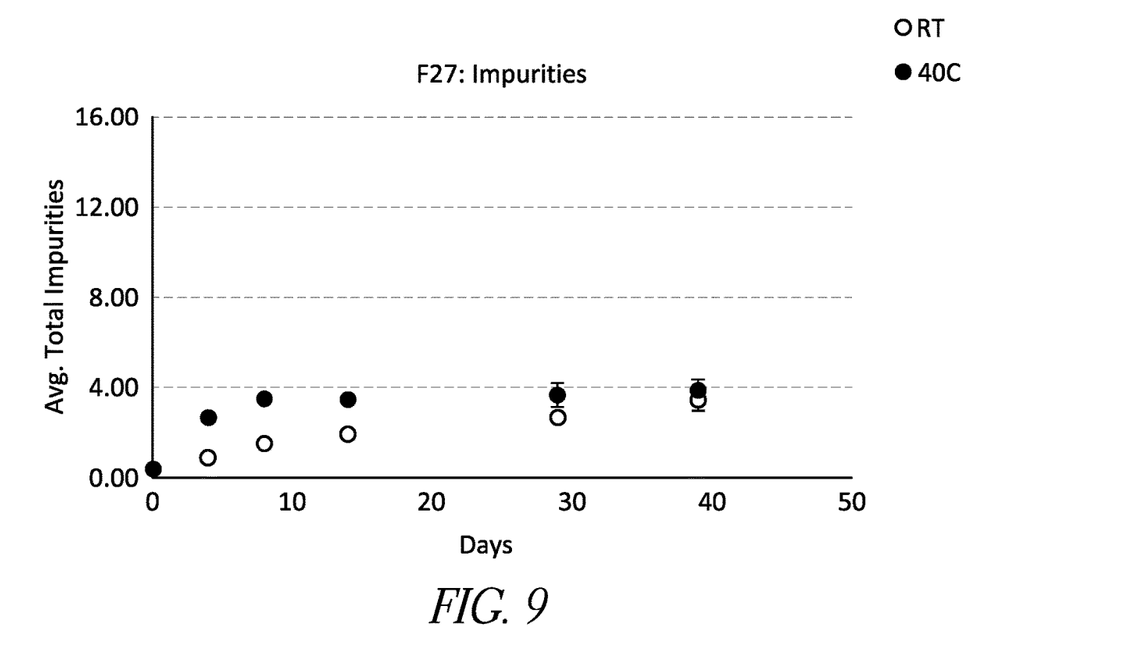
FIG. 9 illustrates stability of an ophthalmic therapeutic treatment composition (F27) having a pH of about 3.5 as a function of storage time at room temperature and 40° C.
Figure 10:
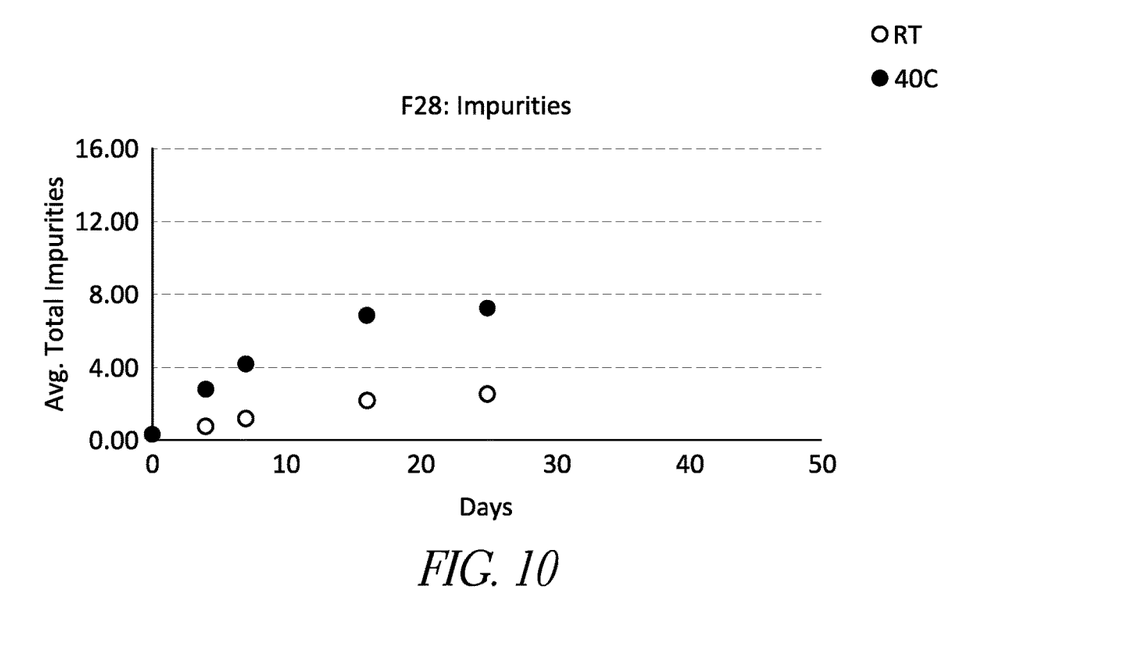
FIG. 10 illustrates stability of an ophthalmic therapeutic treatment composition (F28) having a pH of about 5 as a function of storage time at room temperature and 40° C.

Surprisingly, in some embodiments the combination of crosslinked acrylic acid polymer and acrylamide/sodium acryloyldimethyl taurate copolymer provides unexpectedly high levels of physical stability and API chemical stability, particularly when stored at a pH less than 5. In various embodiments, the degradation of the ophthalmic therapeutic treatment composition is measured at 40° C. or at room temperature. Room temperature is a temperature in the range of about 15° C. to about 25° C. In some embodiments, room temperature is 25° C. The degradation may be accelerated at 40° C. as compared to the degradation at room temperature. For example, FIG. 5 illustrates chemical stability of an ophthalmic therapeutic treatment composition (F2) having a pH of about 5 as a function of storage time at room temperature and 40° C. The illustrated impurities are degradation products of pilocarpine. In contrast, FIG. 6 illustrates the greatly improved stability data for another ophthalmic therapeutic treatment composition (F15) at pH 3.5 instead of pH 5. Similar trends were observed in evaluations of ophthalmic therapeutic treatment composition (F23) at pH 3.5 (FIG. 7) as compared to otherwise identical formulation (F24) at pH 5 (FIG. 8). Likewise, the stability data for ophthalmic therapeutic treatment composition (F27) at pH 3.5 (FIG. 9) is greatly improved as compared to otherwise identical formulation (F28) at pH 5 (FIG. 10). Table 3 summarizes the primary ingredients and pH of the formulations. Amounts shown are for wt % of the indicated ingredient.

TABLE 3

| No. | Carbomer (wt. %) | SEPINEO ® (wt. %) | Pilocarpine (wt. %) | pH |
|---|---|---|---|---|
| F2 | 4 | 0 | 4 | 5 |
| F15 | 2 | 0 (used 2% HPC) | 4 | 3.5 |
| F21 | 2 | 4 | 4 | 3.5 |
| F22 | 2 | 4 | 4 | 5 |
| F23 | 4 | 4 | 4 | 3.5 |
| F24 | 4 | 4 | 4 | 5 |
| F25 | 2 | 4 | 8 | 3.5 |
| F26 | 2 | 4 | 8 | 5 |
| F27 | 4 | 4 | 8 | 3.5 |
| F28 | 4 | 4 | 8 | 5 |
| F29 | 3 | 3 | 4 | 3.5 |
| F30 | 3 | 3 | 8 | 3.5 |

In various embodiments, the ophthalmic therapeutic treatment composition has less than about 5% (w/w) of degradation of the API when measured after storage at 40° C. for 60 days after preparation of the ophthalmic therapeutic treatment composition. In some embodiments, ophthalmic therapeutic treatment composition has less than about 4.5% (w/w) of degradation of the API when measured after storage at 40° C. for 60 days after preparation of the ophthalmic therapeutic treatment composition. In some embodiments, ophthalmic therapeutic treatment composition has less than about 4% (w/w) of degradation of the API when measured after storage at 40° C. for 30 days after preparation of the ophthalmic therapeutic treatment composition. In an embodiment, the ophthalmic therapeutic treatment composition has less than about 10% (w/w) of degradation of the API when measured after storage at 40° C. for 4 months after preparation of the ophthalmic therapeutic treatment composition.

The ophthalmic therapeutic treatment composition includes an effective amount of an active pharmaceutical ingredient (API) dispersed in the topical cream. In an embodiment, the ophthalmic therapeutic treatment composition comprises about 0.001% to about 10% (w/w) of the API. In some embodiments, the API comprises pilocarpine, travoprost, atropine, donepezil, physostigmine or combinations thereof. In some embodiments, the API can be pilocarpine, travoprost, atropine, donepezil, physostigmine or combinations thereof. For example, in an embodiment, the ophthalmic therapeutic treatment composition comprises about 0.004% to about 10% (w/w), about 1% to about 8% (w/w) or about 2% to about 8% (w/w) of the API. For any particular API, the effective amount in the composition may be adjusted based on the disease or disorder for which treatment is indicated. For example, in an embodiment, the API is pilocarpine and effective amounts are typically in the range of about 1% to about 8% (w/w). In an embodiment, the ophthalmic therapeutic treatment composition comprises an amount of the API (e.g., pilocarpine) that is effective to alleviate the symptoms of dry eye. In an embodiment, the ophthalmic therapeutic treatment composition comprises an amount of the API (e.g., pilocarpine) that is effective to treat presbyopia. In an embodiment, the API comprises travoprost. In an embodiment, the ophthalmic therapeutic treatment composition comprises an amount of the API (e.g., travoprost) that is effective to treat intraocular pressure (IOP). In an embodiment, the API comprises physostigmine. In an embodiment, the ophthalmic therapeutic treatment composition comprises an amount of the API (e.g., physostigmine) that is effective to treat blepharitis. In an embodiment, the API comprises donepezil. In an embodiment, the ophthalmic therapeutic treatment composition comprises an amount of the API (e.g., donepezil) that is effective to treat blepharitis.

The ophthalmic therapeutic treatment compositions disclosed herein can be prepared in various ways, e.g., by intimate mixing of the various ingredients to thereby form a topical cream. In an embodiment, the acrylamide/sodium acryloyldimethyl taurate copolymer is added to the other ingredients and mixed well prior to adding the crosslinked acrylic acid polymer. When EDTA is present in the formulation, it was found that the opposite order of mixing (i.e., adding the crosslinked acrylic acid polymer first and then the acrylamide/sodium acryloyldimethyl taurate copolymer) resulted in the formation of EDTA microcrystals. In another embodiment, when a strong base (such as NaOH) is used to adjust the pH of the ophthalmic therapeutic treatment composition, the strong base is added to the other ingredients and mixed well prior to adding the API. It was found that the opposite order of addition (i.e., adding the strong base to the other ingredients after adding the API) resulted in higher levels of API degradation.

In various embodiments, the ophthalmic therapeutic treatment composition is sterilized. For example, in an embodiment, the ophthalmic therapeutic treatment composition is sterilized by e-beam treatment. As indicated by the data in Table 4, such e-beam sterilization tended to enhance the viscosity of the ophthalmic therapeutic treatment composition somewhat, but the viscosity remained in a desirable range.

TABLE 4

| | Viscosity values of pilocarpine formulations before and after e-Beam (25 kGy) sterilization | |
|---|---|---|
| | 4% Pilocarpine | 8% Pilocarpine |
| Before eBeam | 15930 cPs | 10330 cPs |
| After eBeam | 23980 cPs | 16780 cPs |

Methods of Treatment

Various embodiments provide methods of treating a disease or disorder of the eye by topical administration of an ophthalmic therapeutic treatment composition as described herein.

For example, an embodiment provides a method for administering an ophthalmic medicine to a patient's eye, the method comprising applying an ophthalmic therapeutic treatment composition to an outer surface of an eyelid of the patient's eye, wherein the ophthalmic therapeutic treatment composition comprises a topical cream comprising about 0.5% to about 8% (w/w) of a crosslinked acrylic acid polymer and about 0.25% to about 8% (w/w) an acrylamide/ sodium acryloyldimethyl taurate copolymer; and an effective amount of an active pharmaceutical ingredient (API) dispersed in the topical cream. The amounts and types of the various ingredients and the indications are described above with respect to the ophthalmic therapeutic treatment compositions.

In various embodiments, the API is pilocarpine and the method of treatment is effective to alleviate the symptoms of dry eye. In another embodiment, the API is pilocarpine) and the method of treatment is effective to treat presbyopia. In an embodiment, the API comprises travoprost and the method of treatment is effective to treat intraocular pressure (IOP). In an embodiment, the API comprises physostigmine or donepezil and the method of treatment is effective to treat blepharitis. In an embodiment, the API comprises travoprost or pilocarpine and the method of treatment is effective to treat blepharitis.

In an embodiment, the method comprises applying the ophthalmic therapeutic treatment composition to the outer surface of the eyelid of the patient's eye by applying with an applicator. For example, in an embodiment, the treatment comprises squeezing the ophthalmic therapeutic treatment composition from a container onto the applicator (such as a tube attached to the container) and then using the applicator to apply the ophthalmic therapeutic treatment composition to the outer surface of the eyelid of the patient's eye, e.g., by further squeezing the container to push the ophthalmic therapeutic treatment composition from the applicator onto the eyelid.

In various embodiments, the method of treatment comprises applying the ophthalmic therapeutic treatment composition to the outer surface of the eyelid of the patient's eye at least once per day. For example, in an embodiment, the method comprises applying the ophthalmic therapeutic treatment composition to the outer surface of the eyelid of the patient's eye up to four times per day, such as once per day, twice per day, three times per day or four times per day.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the disclosure.

EXAMPLE EMBODIMENTS

1. An ophthalmic therapeutic treatment composition, comprising:
   a topical cream comprising about 0.0% to about 8% (w/w) of a crosslinked acrylic acid polymer and about 0.0% to about 8% (w/w) of an acrylamide/sodium acryloyldimethyl taurate copolymer; and
   an effective amount of an active pharmaceutical ingredient (API) dispersed in the topical cream.

2. The ophthalmic therapeutic treatment composition of Embodiment 1, wherein the ophthalmic therapeutic treatment composition comprises about 0.001% to about 10% (w/w) of the API.

3. The ophthalmic therapeutic treatment composition of Embodiment 2, wherein the ophthalmic therapeutic treatment composition comprises about 2% to about 8% (w/w) of the API.

4. The ophthalmic therapeutic treatment composition of any one of Embodiments 1 to 3, wherein the topical cream comprises about 2% to about 4% (w/w) of the crosslinked acrylic acid polymer.

5. The ophthalmic therapeutic treatment composition of any one of Embodiments 1 to 4, wherein the topical cream comprises about 2% to about 4% (w/w) of the acrylamide/sodium acryloyldimethyl taurate copolymer.

6. The ophthalmic therapeutic treatment composition of any one of Embodiments 1 to 5, wherein the acrylamide/sodium acryloyldimethyl taurate copolymer is dispersed in isohexadecane with polysorbate 80.

7. The ophthalmic therapeutic treatment composition of any one of Embodiments 1 to 6, wherein the API comprises pilocarpine.

8. The ophthalmic therapeutic treatment composition of Embodiment 7, wherein the ophthalmic therapeutic treatment composition comprises an amount of the API that is effective to alleviate the symptoms of dry eye and/or treat presbyopia.

9. The ophthalmic therapeutic treatment composition of any one of Embodiments 1 to 6, wherein the API comprises travoprost.

10. The ophthalmic therapeutic treatment composition of Embodiment 9, wherein the ophthalmic therapeutic treatment composition comprises an amount of the API that is effective to treat intraocular pressure (IOP).

11. The ophthalmic therapeutic treatment composition of any one of Embodiments 1 to 6, wherein the API comprises physostigmine and/or donepezil.

12. The ophthalmic therapeutic treatment composition of Embodiment 11, wherein the ophthalmic therapeutic treatment composition comprises an amount of the API that is effective to treat blepharitis.

13. The ophthalmic therapeutic treatment composition of any one of Embodiments 1 to 12, wherein the ophthalmic therapeutic treatment composition has a pH that is in a range of about 3.0 to about 7.8.

14. The ophthalmic therapeutic treatment composition of Embodiment 13, wherein the pH of the ophthalmic therapeutic treatment composition is in a range of about 3.5 to about 5.5.

15. The ophthalmic therapeutic treatment composition of any one of Embodiments 1 to 14, wherein the ophthalmic therapeutic treatment composition has a viscosity in a range of about 4,000 cPs to about 400,000 cPs.

16. The ophthalmic therapeutic treatment composition of Embodiment 15, wherein the viscosity of the ophthalmic therapeutic treatment composition is in a range of about 5,000 cPs to about 300,000 cPs.

17. The ophthalmic therapeutic treatment composition of any one of Embodiments 1 to 11, wherein the ophthalmic therapeutic treatment composition has a viscosity in a range of about 7,500 cPs to about 250,000 cPs.

18. The ophthalmic therapeutic treatment composition of any one of Embodiments 1 to 17, wherein the ophthalmic therapeutic treatment composition is thixotropic.

19. The ophthalmic therapeutic treatment composition of any one of Embodiments 1 to 18, wherein the ophthalmic therapeutic treatment composition has less than about 5% (w/w) of degradation of the API when measured after storage at 40° C. for 60 days after preparation of the ophthalmic therapeutic treatment composition.

20. The ophthalmic therapeutic treatment composition of any one of Embodiments 1 to 19, wherein the ophthalmic therapeutic treatment composition has less than about 10% (w/w) of degradation of the API when measured after storage at 40° C. for 4 months after preparation of the ophthalmic therapeutic treatment composition.

21. The ophthalmic therapeutic treatment composition of any one of Embodiments 1 to 20, wherein the ophthalmic therapeutic treatment composition is formulated for application to an outer surface of an eyelid to deliver the API into an eye.

22. The ophthalmic therapeutic treatment composition of Embodiment 21, wherein there is less residual of the ophthalmic therapeutic treatment composition after the application of the ophthalmic therapeutic treatment composition to the outer surface of the eyelid compared to application of an otherwise identical composition comprising a hydroxypropyl cellulose (HPC) in place of the acrylamide/sodium acryloyldimethyl taurate copolymer.

23. A method for administering an ophthalmic medicine to a patient's eye, the method comprising applying an ophthalmic therapeutic treatment composition to an outer surface of an eyelid of the patient's eye,
wherein the ophthalmic therapeutic treatment composition comprises a topical cream comprising about 0.5% to about 8% (w/w) of a crosslinked acrylic acid polymer and about 0.25% to about 8% (w/w) an acrylamide/sodium acryloyldimethyl taurate copolymer; and an effective amount of an active pharmaceutical ingredient (API) dispersed in the topical cream.

24. The method of Embodiment 23, wherein the effective amount of the API is about 0.001% to about 10% (w/w).

25. The method of Embodiment 23 or 24, wherein the API comprises pilocarpine, travoprost, atropine, donepezil, or physostigmine.

26. The method of any one of Embodiments 23 to 25, wherein the method comprises applying the ophthalmic therapeutic treatment composition to the outer surface of the eyelid of the patient's eye at least once per day.

27. The method of Embodiment 26, wherein the method comprises applying the ophthalmic therapeutic treatment composition to the outer surface of the eyelid of the patient's eye up to four times per day.

28. The method of any one of Embodiments 23 to 27, wherein applying the ophthalmic therapeutic treatment composition to the outer surface of the eyelid of the patient's eye comprises applying with an applicator.

29. The method of Embodiment 28, wherein the method further comprises squeezing the ophthalmic therapeutic treatment composition from a container onto the applicator before applying the ophthalmic therapeutic treatment composition to the outer surface of the eyelid of the patient's eye.

What is claimed is:

1. An ophthalmic therapeutic treatment composition, comprising:
a topical cream comprising 0.05% to 8% (w/w) of a crosslinked acrylic acid polymer and 0.025% to 8% (w/w) of an acrylamide/sodium acryloyldimethyl taurate copolymer; and
0.001% to 10% (w/w) of an active pharmaceutical ingredient (API) dispersed in the topical cream;
wherein the pH of the ophthalmic therapeutic treatment composition is about 3.5; and
wherein the ophthalmic therapeutic treatment composition is formulated for application to an outer surface of an eyelid to deliver the API into an eye.

2. The ophthalmic therapeutic treatment composition of claim 1, wherein the ophthalmic therapeutic treatment composition comprises 2% to 8% (w/w) of the API.

3. The ophthalmic therapeutic treatment composition of claim 1, wherein the topical cream comprises 2% to 4% (w/w) of the crosslinked acrylic acid polymer.

4. The ophthalmic therapeutic treatment composition of claim 1, wherein the topical cream comprises 2% to 4% (w/w) of the acrylamide/sodium acryloyldimethyl taurate copolymer.

5. The ophthalmic therapeutic treatment composition of claim 1, wherein the acrylamide/sodium acryloyldimethyl taurate copolymer is dispersed in isohexadecane with polysorbate 80.

6. The ophthalmic therapeutic treatment composition of claim 1, wherein the API comprises pilocarpine.

7. The ophthalmic therapeutic treatment composition of claim 1, wherein the ophthalmic therapeutic treatment composition comprises 0.004% to 10% (w/w) of the API.

8. The ophthalmic therapeutic treatment composition of claim 1, wherein the API comprises travoprost.

9. The ophthalmic therapeutic treatment composition of claim 1, wherein the API comprises atropine.

10. The ophthalmic therapeutic treatment composition of claim 1, wherein the API comprises donepezil.

11. The ophthalmic therapeutic treatment composition of claim 1, wherein the API comprises physostigmine.

12. The ophthalmic therapeutic treatment composition of claim 1, wherein the ophthalmic therapeutic treatment composition has a viscosity in a range of 4,000 cPs to 400,000 cPs.

13. The ophthalmic therapeutic treatment composition of claim 1, wherein the ophthalmic therapeutic treatment composition has a viscosity in a range of 7,500 cPs to 250,000 cPs.

14. The ophthalmic therapeutic treatment composition of claim 1, wherein the ophthalmic therapeutic treatment composition is thixotropic.

15. The ophthalmic therapeutic treatment composition of claim 1, wherein the ophthalmic therapeutic treatment composition has less than 5% (w/w) of degradation of the API when measured after storage at 40° C. for 60 days after preparation of the ophthalmic therapeutic treatment composition.

16. The ophthalmic therapeutic treatment composition of claim 1, wherein there is less residual of the ophthalmic therapeutic treatment composition after the application of the ophthalmic therapeutic treatment composition to the outer surface of the eyelid compared to application of an otherwise identical composition comprising a hydroxypropyl cellulose (HPC) in place of the acrylamide/sodium acryloyldimethyl taurate copolymer.

17. The ophthalmic therapeutic treatment composition of claim 1, wherein the pH is 3.5.

18. A method for administering an ophthalmic medicine to a patient's eye, the method comprising applying an ophthalmic therapeutic treatment composition to an outer surface of an eyelid of the patient's eye, wherein the ophthalmic therapeutic treatment composition comprises a topical cream comprising 0.5% to 8% (w/w) of a crosslinked acrylic acid polymer and 0.25% to 8% (w/w) an acrylamide/sodium acryloyldimethyl taurate copolymer; wherein the pH of the ophthalmic therapeutic treatment composition is of about 3.5; and an effective amount of an active pharmaceutical ingredient (API) dispersed in the topical cream.

19. The method of claim 18, wherein the pH is 3.5.

* * * * *